United States Patent
Yorimoto et al.

(10) Patent No.: US 9,968,410 B2
(45) Date of Patent: May 15, 2018

(54) TREATMENT TOOL

(71) Applicant: OLYMPUS CORPORATION, Tokyo (JP)

(72) Inventors: Ryuichi Yorimoto, Tokyo (JP); Masatoshi Iida, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 289 days.

(21) Appl. No.: 14/860,941

(22) Filed: Sep. 22, 2015

(65) Prior Publication Data
US 2016/0074121 A1   Mar. 17, 2016

Related U.S. Application Data

(63) Continuation of application No. PCT/JP2014/057878, filed on Mar. 20, 2014.
(Continued)

(51) Int. Cl.
*A61B 19/00* (2006.01)
*A61B 34/30* (2016.01)
(Continued)

(52) U.S. Cl.
CPC .......... *A61B 34/30* (2016.02); *A61B 19/2203* (2013.01); *A61B 34/71* (2016.02);
(Continued)

(58) Field of Classification Search
CPC ... B25J 9/08; B25J 9/104; B25J 13/086; B25J 13/088; B25J 15/0206; A61B 34/30; A61B 34/71
(Continued)

(56) References Cited

U.S. PATENT DOCUMENTS 4,600,357 A * 7/1986 Coules .................. B25J 13/082
                                                          294/106
8,105,338 B2   1/2012 Anderson et al.
(Continued)

FOREIGN PATENT DOCUMENTS

JP   H06-183684 A   7/1994
JP   2003-024336 A   1/2003
(Continued)

OTHER PUBLICATIONS

International Search Report dated Jun. 17, 2014 issued in PCT/JP2014/057878.
(Continued)

*Primary Examiner* — William C Joyce
(74) *Attorney, Agent, or Firm* — Scully, Scott, Murphy & Presser, P.C.

(57) ABSTRACT

The endoscope treatment system includes an endoscope treatment tool that has an operating part having a distal end and a proximal end, and a sheath that is connected to the distal end of the operating part and is formed with a lumen through that enables a guide wire to be inserted therethrough; a guide wire holder around which a tube member housing the guide wire is wound circumferentially; and a fixing member that couples the operating part to the guide wire holder such that the distal end and the proximal end of the operating part are located outside the circumference of the guide wire holder.

12 Claims, 11 Drawing Sheets

Related U.S. Application Data

(60) Provisional application No. 61/805,256, filed on Mar. 26, 2013.

(51) Int. Cl.
  *A61B 34/00*  (2016.01)
  *A61B 90/00*  (2016.01)
  *A61B 17/00*  (2006.01)
  *A61B 34/20*  (2016.01)

(52) U.S. Cl.
  CPC .............. *A61B 2017/00323* (2013.01); *A61B 2017/00477* (2013.01); *A61B 2019/2238* (2013.01); *A61B 2019/4857* (2013.01); *A61B 2034/2057* (2016.02); *A61B 2034/2061* (2016.02); *A61B 2034/301* (2016.02); *A61B 2034/306* (2016.02); *A61B 2090/061* (2016.02); *A61B 2090/0811* (2016.02)

(58) Field of Classification Search
  USPC ............. 74/490.01, 490.03; 901/31, 35, 46
  See application file for complete search history.

(56) References Cited

U.S. PATENT DOCUMENTS

| | | |
|---|---|---|
| 2009/0024141 A1 | 1/2009 | Stahler et al. |
| 2010/0241135 A1 | 9/2010 | Iida |
| 2012/0130400 A1 | 5/2012 | Brock et al. |
| 2012/0152045 A1 | 6/2012 | Isobe et al. |
| 2014/0039519 A1* | 2/2014 | Inoue ............... A61B 19/2203 606/130 |
| 2014/0117689 A1* | 5/2014 | Davis ................ B25J 15/0028 294/192 |

FOREIGN PATENT DOCUMENTS

| | | |
|---|---|---|
| JP | 2010-220684 A | 10/2010 |
| JP | 2012-235936 A | 12/2012 |
| JP | 2014-028007 A | 2/2014 |
| WO | 2007/146987 A2 | 12/2007 |
| WO | WO 2012/153871 A1 | 11/2012 |

OTHER PUBLICATIONS

Extended Supplementary European Search Report dated Oct. 4, 2016 in related European Patent Application No. 14 77 6095.3.

* cited by examiner

TREATMENT TOOL

This application is a continuation claiming priority on the basis of U.S. Patent Application No. 61/805,256 provisionally applied in US on Mar. 26, 2013 and based on PCT/JP2014/057878 filed on Mar. 20, 2014. The contents of both the PCT application and the U.S. Provisional Application are incorporated herein by reference.

TECHNICAL FIELD

The present invention relates to a treatment tool.

BACKGROUND ART

In the related art, treatment tools having a movable part at a distal end of a bendable elongated insertion part are known as surgical equipment for performing surgical procedures, such as excision of lesions. Additionally, treatment tools which actuate the movable part provided at the distal end of the insertion part with a driving force exerted from a driving source, such as a servo motor, are known. The treatment tools that actuate the movable part with the driving force exerted from the driving source are configured such that the driving force is transmitted to the movable part by a power-transmitting member, such as a wire disposed along the insertion part. The movable part is controlled to make a desired movement on the basis of the amount of displacement of the movable part detected by a detecting part.

U.S. Pat. No. 8,105,338 discloses a treatment tool in which a treatment-tool-side unit and a drive-unit-side unit having a driving source are detachably coupled together. In the treatment tool described in U.S. Pat. No. 8,105,338, an output part of a driving source and an input part to which the output of the driving source is input to the power-transmitting member are detachably coupled together via a coupling.

SUMMARY OF THE INVENTION

According to a first aspect of the present invention, a treatment tool includes a treatment tool unit having a treatment tool body part and a treatment tool base part; and a drive unit that is detachably combined with the treatment tool base part of the treatment tool unit. The treatment tool body part includes a movable part that is displaced; an insertion part having the movable part; and a driving force transmission member that has a distal end coupled to the movable part, has a proximal end guided to a proximal end side of the insertion part along the insertion part, and transmits a driving force to the movable part to displace the movable part by the driving force being input from the outside to the proximal end; and a displacement amount transmission member that has a distal end coupled to at least one of the driving force transmission member and the movable part, has a proximal end guided to the proximal end side of the insertion part along the insertion part, and transmits the amount of displacement thereof to the proximal end when the movable part has been displaced. The treatment tool base part includes a treatment-tool-unit-side base member that has the proximal end side of the insertion part combined therewith; a driving force input part that is provided in a treatment-tool-unit-side base member, and inputs the driving force from the outside for displacing the movable part to the proximal end of the driving force transmission member; and a displacement amount detected part that is provided at the proximal end of the displacement amount transmission member and is displaced along a given direction by an amount according to the amount of displacement transmitted to the proximal end of the displacement amount transmission member. The drive unit includes a driving source that generates a driving force that actuates the movable part; and a drive-unit-side base member that supports the driving source and has the treatment-tool-unit-side base member of the treatment tool base part detachably coupled thereto. A power transmission joint that detachably couples an output part of the driving source and the driving force input part in a state where power transmission is allowed from the output part of the driving source to the driving force input part when the treatment-tool-unit-side base member is coupled to the drive-unit-side base member, and a displacement amount detecting part that is brought into a state where the amount of displacement of the displacement amount detected part is detectable and that is brought into a state where a detection signal is outputtable from the drive unit side when the treatment-tool-unit-side base member is coupled to the drive-unit-side base member are provided between the treatment tool unit and the drive unit.

According to a second aspect of the present invention based on the first aspect, the displacement amount detected part may be provided so as to be movable along a direction parallel to a combined surface of the treatment-tool-unit-side base member combined with the drive-unit-side base member, and the displacement amount detecting part may be provided as a displacement amount detecting part for detecting the amount of displacement of the displacement amount detected part in a contactless manner with respect to the displacement amount detected part, at a position on the drive unit side that faces the displacement amount detected part when the treatment-tool-unit-side base member and the drive-unit-side base member are coupled together.

According to a third aspect of the present invention based on the second aspect, the treatment tool unit may be provided with a positioning portion that positions the displacement amount detecting part with respect to the displacement amount detected part, and the drive unit may be provided with a biasing part for biasing and positioning the displacement amount detecting part provided in the drive unit to the positioning portion provided in the treatment tool unit when the treatment-tool-unit-side base member and the drive-unit-side base member are coupled together.

According to a fourth aspect of the present invention based on the second aspect, the treatment tool unit may be provided with a positioning portion that positions the displacement amount detecting part with respect to the displacement amount detected part as the displacement amount detecting part provided in the drive unit is fitted to the positioning portion when the treatment-tool-unit-side base member and the drive-unit-side base member are coupled together.

According to a fifth aspect of the present invention based on the second aspect, the size of the displacement amount detected part may be set to be greater than an expected connection error in a direction along combined surfaces of the treatment-tool-unit-side base member and the drive-unit-side base member when the treatment-tool-unit-side base member and the drive-unit-side base member are coupled together.

According to a sixth aspect of the present invention based on the first aspect, the displacement amount detecting part may be provided at the position of the treatment tool unit that faces the displacement amount detected part, the treatment tool unit may be provided with a transmitting unit for the detection signal from the displacement amount detecting part, and a receiving unit capable of receiving the detection signal of the displacement amount detecting part from the transmitting unit and outputting the received detection signal to the position of the drive unit where transfer of the detection signal with the transmitting unit is allowed when the treatment-tool-unit-side base member and the drive-unit-side base member are coupled together.

DESCRIPTION OF EMBODIMENTS

First Embodiment

A treatment tool of a first embodiment of the present invention will be described.

Figure 1:
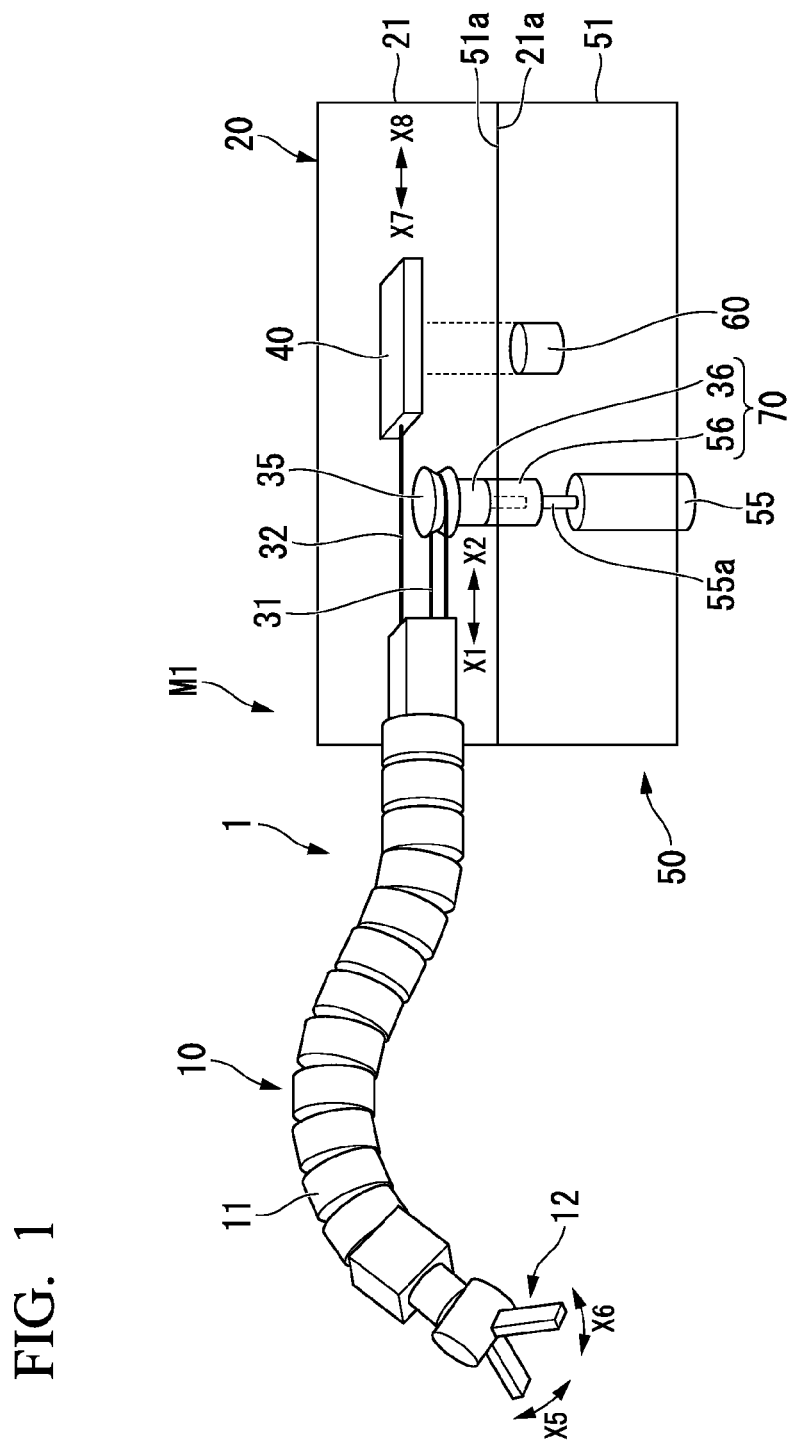
FIG. 1 is a configuration view schematically showing the general outline of a treatment tool of a first embodiment of the present invention.
Figure 2:
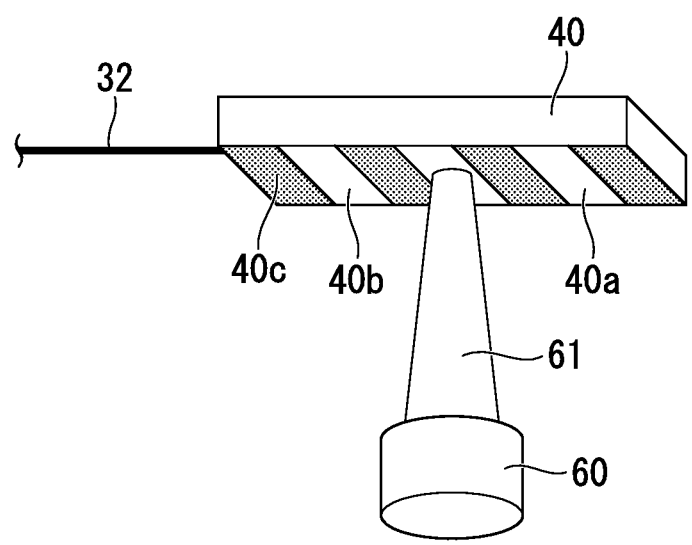
FIG. 2 is a perspective view showing the relationship between a displacement amount detected part and displacement amount detecting part in the treatment tool of the first embodiment of the present invention.
Figure 3:
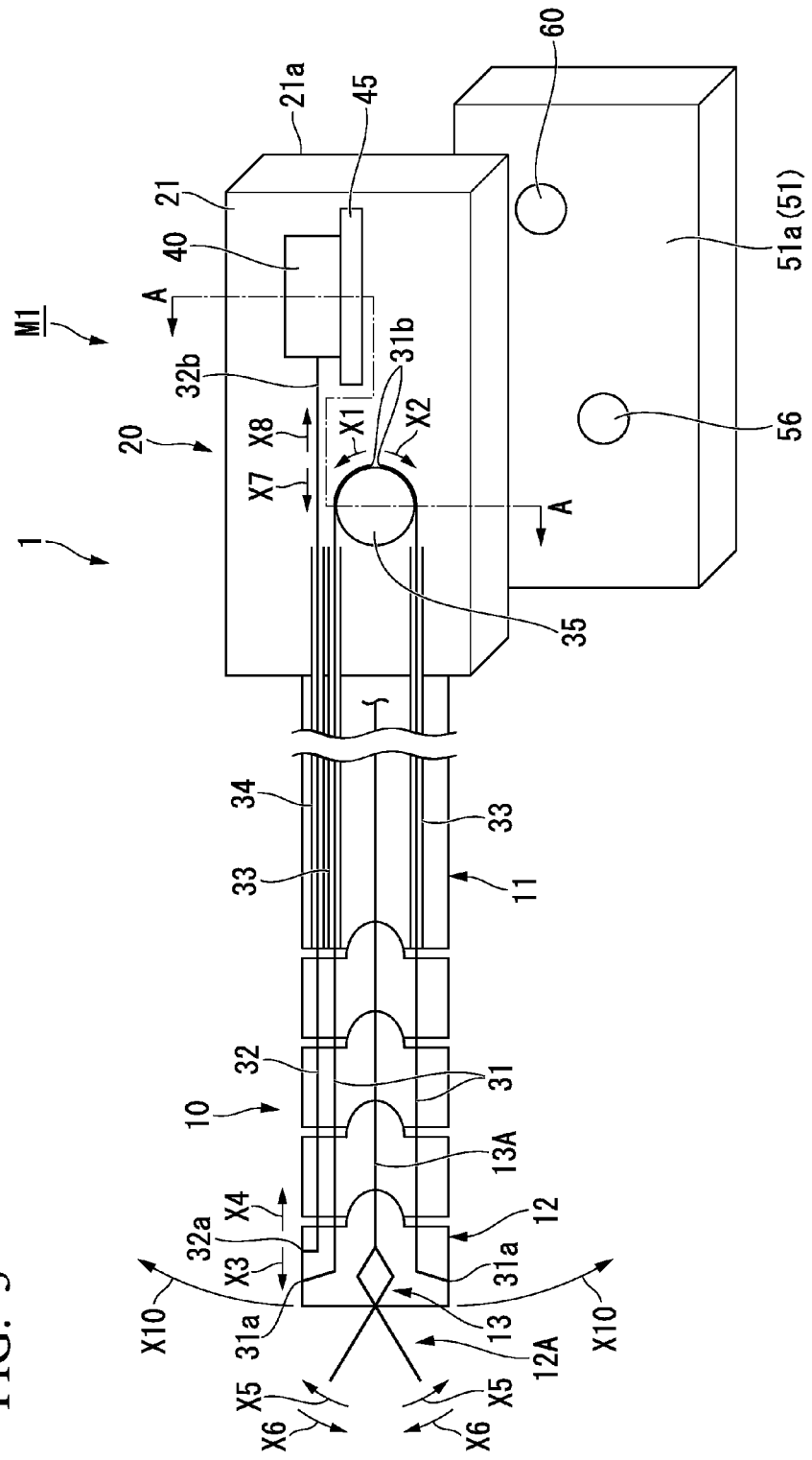
FIG. 3 is a configuration view schematically showing the general outline of the treatment tool of the first embodiment of the present invention.
Figure 4:
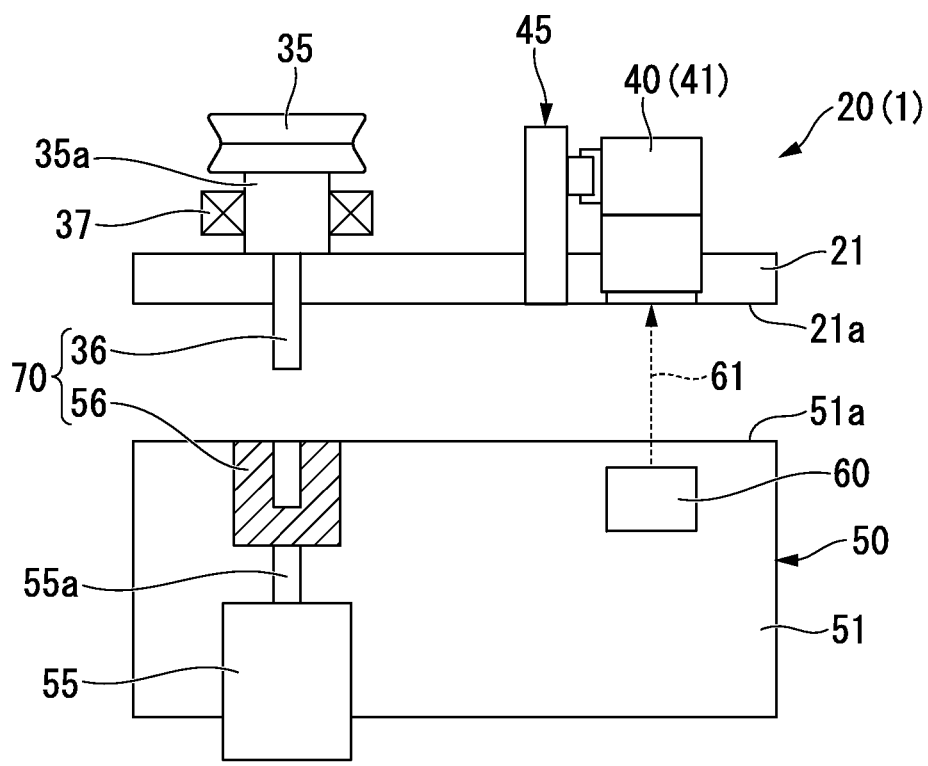
FIG. 4 is a cross-sectional view as seen from arrow A-A of FIG. 3.

FIG. 1 is a configuration view schematically showing the general outline of the treatment tool of the first embodiment of the present invention. FIG. 2 is a perspective view showing the relationship between a displacement amount detected part and a displacement amount detecting part of the treatment tool. FIG. 3 is a configuration view schematically showing the entire general outline of the treatment tool. FIG. 4 is a cross-sectional view as seen from arrow A-A of FIG. 3.

As shown in FIGS. 1 and 3, a treatment tool M1 of the present embodiment includes a treatment tool unit 1 and a drive unit 50. The treatment tool unit 1 includes a treatment tool body part 10 and a treatment tool base part 20. The treatment tool base part 20 of the treatment tool unit 1 is detachably combined with the drive unit 50.

The treatment tool body part 10 has an insertion part 11 having a bendable flexible structure. The insertion part 11 has, for example, a plurality of joints and is freely bent as a whole by being bent in the respective joints. A movable part 12 is provided at the distal end of the insertion part 11. In the present specification, a description will be made with a side where the movable part 12 is provided being defined as a distal end side, and a treatment tool base part 20 side being defined a proximal end side.

As shown in FIG. 3, the movable part 12 in the present embodiment is displaced (is operated to rotate in a direction of arrow X10) with respect to a central axis of the insertion part 11 by the movement (directions of arrows X1 and X2) of a driving wire 31 to be described below. As the movable part 12 is displaced in this way, the insertion part 11 is operated for bending. The movable part 12 is provided with forceps having a gripping part 12A and a link 13. The gripping part 12A of the forceps performs the opening/closing operation (directions of arrows X5 and X6) in accordance with the movement in central axis directions (directions of arrows X3 and X4 direction) of the insertion part 11 using a wire 13A connected to a proximal end of the link 13. The wire 13A is operated by well-known mechanisms, such as a motor (not shown).

The driving wire 31 and a sensing wire 32 are inserted into the insertion part 11. The driving wire 31 and the sensing wire 32 are movable back and forth along a longitudinal axis of the insertion part 11 by being guided by wire guides 33 and 34, respectively.

The driving wire 31 is a driving force transmission member for bending a distal end portion of the insertion part 11. In the present embodiment, two driving wires 31 are inserted into the insertion part 11. A distal end 31a of each driving wire is fixed to the movable part 12 at the distal end of the insertion part 11. A proximal end 31b of each driving wire 31 is fixed to an outer peripheral surface of a pulley 35 provided in the treatment tool base part 20. The driving wire 31 may have a U shape in which both ends are fixed to the movable part 12 at the distal end of the insertion part 11 and an intermediate portion is disposed in the treatment tool base part 20 via the pulley 35.

The distal end 31a of each driving wire 31 is fixed to a position where this distal end faces the movable part 12 at the distal end of the insertion part 11 in a radial direction of the insertion part 11, and if one of the two driving wires 31 is pulled to the proximal end side, the distal end of the insertion part 11 is bent toward the pulled driving wire 31 side.

The sensing wire 32 is a displacement amount transmission member provided to detect the displacement amount of a distal end portion (a portion having the joints) of the movable part 12, that is, the bending amount of the insertion part 11. A distal end 32a of the sensing wire 32 is fixed to the movable part 12 at the distal end of the insertion part 11, and a proximal end of the sensing wire 32 is connected to a displacement amount detected part 40 in the treatment tool base part 20.

The sensing wire 32 has a configuration in which the sensing wire does not receive an unnecessary external force as the elongation of the sensing wire 32 does not influence a proximal end 32b side of the sensing wire 32 to the utmost. For example, the sensing wire 32 may be fixed only to two places of the movable part 12 at the distal end of the insertion part 11 and the displacement amount detected part 40, and portions other than both ends of the sensing wire 32 may have a coating for reducing sliding resistance.

The wire guide 33 is a tubular member having flexibility that defines a path for the driving wire 31 and guides the driving wire 31. The wire guide 33 of the driving wire 31 is formed from, for example, a coil pipe. The wire guide 34 is a tubular member having flexibility that defines a path for the sensing wire 32 and guides the sensing wire 32.

The wire guide 34 of the sensing wire 32 is formed from, for example, a coil pipe or a metallic pipe. Additionally, an inner surface of the wire guide 34 and an outer surface of the sensing wire 32 may be subjected to surface treatment or the like such that the friction therebetween becomes small.

The treatment tool base part 20 includes a treatment-tool-unit-side base member 21 with which the proximal end side of the insertion part 11 of the treatment tool body part 10 is combined. The proximal end 31b of the driving wire 31 is delivered onto the treatment tool base part 20 from the wire guide 33. The treatment-tool-unit-side base member 21 is provided with the pulley (driving force input part) 35 with which the respective proximal ends 31b of the respective driving wires 31 are wound. The pulley 35 is a driving force input part that receives a force (for example, a rotational driving force from the outside) used as a pulling force for the movable part 12 at the distal end of the insertion part 11 and inputs the force to the proximal end 31b of the driving wire 31.

As shown in FIG. 4, the pulley 35 is rotatably supported by the treatment-tool-unit-side base member 21 via a bearing 37. As the pulley 35 rotates, as shown in FIG. 3, the driving wire 31 is pushed in the direction of arrow X1, or is pulled in the direction of arrow X2.

Additionally, as shown in FIG. 3, the proximal end 32b of the sensing wire 32 is delivered on the treatment tool base part 20 from the wire guide 34. The displacement amount detected part 40 is coupled to the proximal end 32b of the sensing wire 32. The displacement amount detected part 40 is a member that is displaced by the amount of displacement transmitted to the proximal end 32b of the sensing wire 32. The displacement amount detected part 40 is slidably supported by the treatment-tool-unit-side base member 21 so as to be displaced in a given direction by a sliding guide mechanism 45.

The drive unit 50 has a drive-unit-side base member 51. The drive-unit-side base member 51 is provided with a drive motor (driving source) 55 that generates a driving force for actuating the movable part 12 of the treatment tool unit 1.

The drive-unit-side base member 51 is provided with a combined surface 51a where the drive-unit-side base member 51 and the treatment-tool-unit-side base member 21 are combined together when the treatment tool unit 1 is coupled to the drive unit 50. Similarly, the treatment-tool-unit-side base member 21 is provided with a combined surface 21a where the drive-unit-side base member 51 and the treatment-tool-unit-side base member 21 are combined together when the treatment tool unit 1 is coupled to the drive unit 50.

The drive unit 50 and the treatment tool unit 1 are combined together with bolts or clamp mechanisms (not shown) in a state where the combined surfaces 51a and 21a of the drive-unit-side base member 51 and the treatment-tool-unit-side base member 21 are combined together.

The drive unit 50 is provided with a displacement amount detecting part 60 that is brought into a state where the amount of displacement of the displacement amount detected part 40 can be detected in a contactless manner when the treatment-tool-unit-side base member 21 is coupled to the drive-unit-side base member 51. The displacement amount detecting part 60 outputs a signal, which is obtained by detecting the amount of displacement of the displacement amount detected part 40, from the drive unit 50 side. For example, the displacement amount detecting part 60 has an optical encoder.

As shown in FIG. 2, the displacement amount detecting part 60 is provided at a position where the displacement amount detecting part faces a detected surface 40a of the displacement amount detected part 40 when the treatment-tool-unit-side base member 21 and the drive-unit-side base member 51 are coupled together. The displacement amount detected part 40 is provided so as to be slidable in a direction parallel to the combined surface 21a of the treatment-tool-unit-side base member 21. The detected surface 40a of the displacement amount detected part 40 is formed as a flat surface parallel to the combined surface 21a of the treatment-tool-unit-side base member 21.

The detected surface 40a of the displacement amount detected part 40 is provided with a high-reflection portion 40b from which detection light 61 is strongly reflected and a low-reflection portion 40c from which the detection light is weakly reflected when the displacement amount detecting part 60 irradiates the detected surface 40a with the detection light 61. The high-reflection portion 40b and the low-reflection portion 40c are alternately arrayed at regular pitches in a sliding direction of the displacement amount detected part 40. Therefore, the displacement amount detecting part 60 can detect the amount of displacement of the displacement amount detected part 40 by counting the intensity of the reflected light when the displacement amount detected part 40 slides.

As shown in FIG. 4, a coupling (power transmission joint) 70, which detachably couples an output shaft (output part) 55a of the drive motor 55 with a rotating shaft 35a of the pulley 35, is provided between the drive unit 50 and the treatment tool base part 20. The coupling 70 is, for example, a concavo-convex fitting type coupling that can transmit rotary power. The coupling 70 is constituted of a first coupling portion 56 that is provided on the output shaft 55a side of the drive motor 55, and a second coupling portion 36 that is provided on the rotating shaft 35a side of the pulley 35. When the treatment-tool-unit-side base member 21 is coupled to the drive-unit-side base member 51, the first coupling portion 56 and the second coupling portion 36 are fitted to each other, and are brought into a state where rotational power can be transmitted from the output shaft 55a of the drive motor 55 to the pulley 35.

Figure 5:
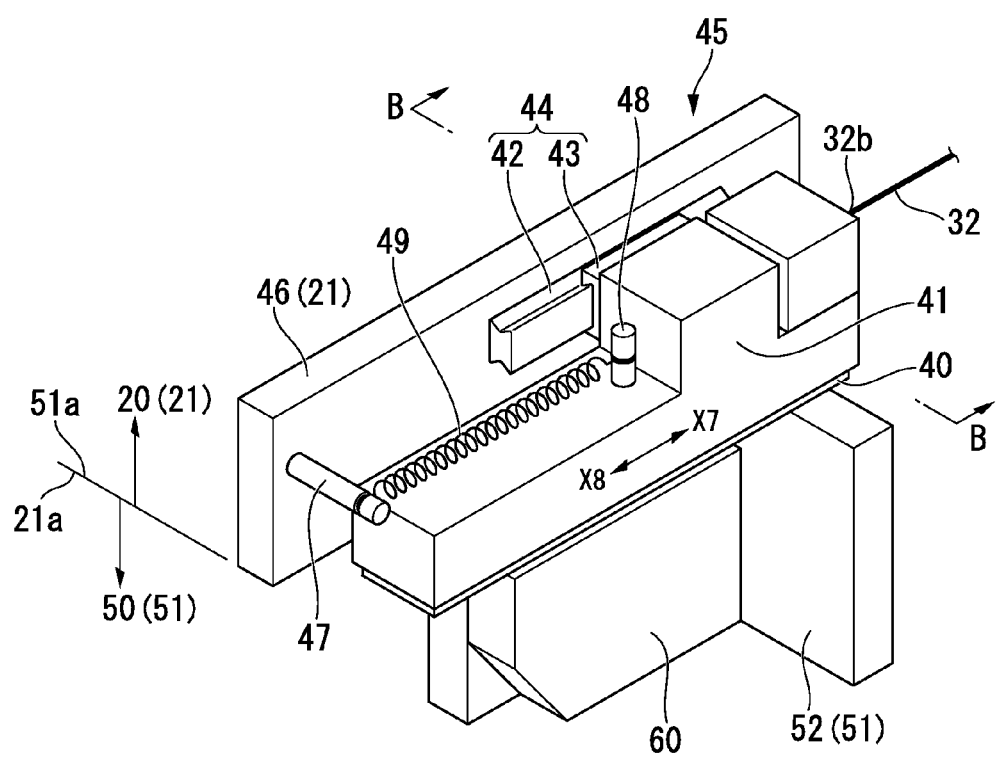
FIG. 5 is a perspective view showing the relationship between the displacement amount detected part and the displacement amount detecting part in the treatment tool of the first embodiment of the present invention.
Figure 6:
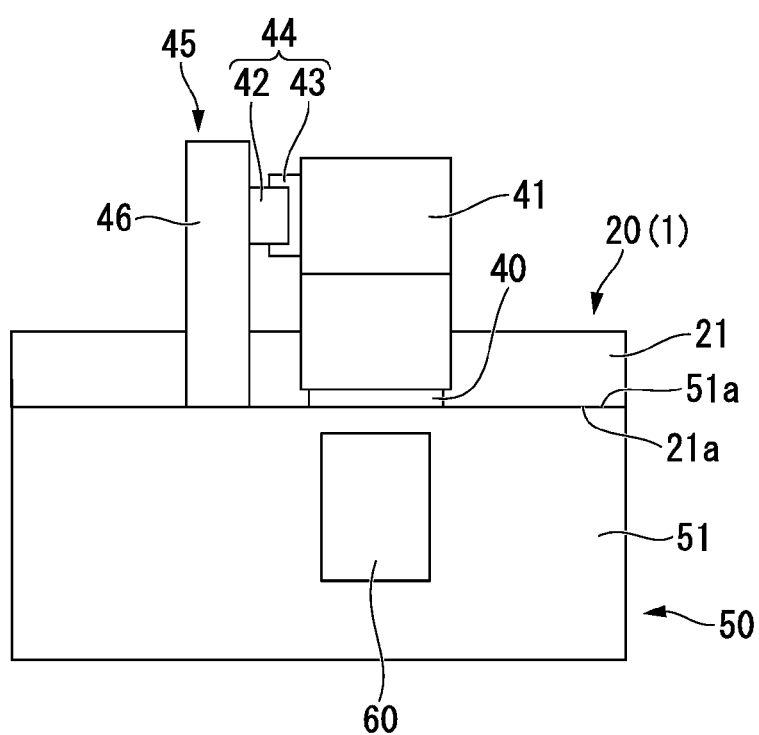
FIG. 6 is a cross-sectional view as seen from arrow B-B of FIG. 5.

FIG. 5 is a perspective view showing the relationship between the displacement amount detected part 40 and the displacement amount detecting part 60 in the treatment tool M1 of the embodiment. FIG. 6 is a cross-sectional view as seen from arrow B-B of FIG. 5. As shown in FIGS. 5 and 6, the treatment-tool-unit-side base member 21 is provided with a bracket 46. A sliding member 41 is attached to the bracket 46 via a sliding guide mechanism 45. The displacement amount detected part 40 is provided parallel to the sliding direction of the sliding member 41 and parallel to the combined surface 21a of the treatment-tool-unit-side base member 21, in the sliding member 41.

The sliding guide mechanism 45 is constituted of a linear guide mechanism 44 having a guide rail 42 that is fixed to the bracket 46 and a slider 43 that is linearly guided along the guide rail 42. The sliding member 41 provided with the displacement amount detected part 40 is attached to the slider 43 of the linear guide mechanism 44. Accordingly, the sliding member 41 is slidably supported by the treatment-tool-unit-side base member 21 via the sliding guide mechanism 45 in directions (directions of arrows X7 and X8) in which the guide rail 42 of the linear motion guide mechanism 44 extends.

Additionally, a pulling spring 49 is provided between a pin 47 fixed to the bracket 46 and a pin 48 fixed to the sliding member 41. Accordingly, the sliding member 41 is always biased such that the sensing wire 32 is pulled to the proximal end side (direction of arrow X8). The proximal end 32b of the sensing wire 32 is coupled to an end portion of the sliding member 41 on the distal end side (arrow X7 side). The sensing wire 32 is held in a state where loosening is removed due to the pulling force of the pulling spring 49. The magnitude of the pulling force of the pulling spring 49 is set to such a degree that the sliding member 41 can move to the distal end side along the guide rail 42 with the pulling force transmitted via the driving wire 31, the movable part 12, the sensing wire 32, and the sliding member 41 from the drive motor 55.

The displacement amount detecting part 60 is attached to the drive-unit-side base member 51 via a bracket 52. A detecting part (part that emits the detection light 61 and receives reflected light) of the displacement amount detecting part 60 can irradiate the detected surface 40a (refer to FIG. 2) of the displacement amount detected part 40 with the detection light 61 when the treatment-tool-unit-side base member 21 and the drive-unit-side base member 51 are coupled together.

The operation of the treatment tool M1 of the present embodiment will be described.

When the treatment tool M1 is used, a user combines the treatment tool base part 20 of the treatment tool unit 1 with the drive unit 50. This combination is performed in a state where the combined surface 21a of the treatment-tool-unit-side base member 21 and the combined surface 51a of the drive-unit-side base member 51 are combined together. If the treatment-tool-unit-side base member 21 and the drive-unit-side base member 51 are coupled together, the first coupling portion 56 and the second coupling portion 36 of the coupling 70 are coupled together. Accordingly, a state where the rotational driving force of the drive motor 55 can be transmitted to the pulley 35 is brought about.

Additionally, if the treatment-tool-unit-side base member 21 and the drive-unit-side base member 51 are coupled together, the detecting part of the displacement amount detecting part 60 on the drive unit 50 side faces the displacement amount detected part 40 of the treatment tool base part 20. Therefore, the displacement amount detecting part 60 is brought into a state where the amount of displacement of the displacement amount detected part 40 in the sliding direction can be detected.

In this state, if the drive motor 55 rotates, the rotation of the drive motor 55 is transmitted to the pulley 35. If the pulley 35 rotates, the driving wire 31 is operated to move back and forth in the direction of arrow X1 and X2 of FIG. 3. If the driving wire 31 is operated to move back and forth, the distal end portion of the insertion part 11 is operated for bending in the direction of arrow X10.

On the other hand, if the distal end portion of the insertion part 11 is operated for bending in the direction of arrow X10, the sliding member 41 and the displacement amount detected part 40 are displaced in the directions of arrows X7 and X8 together with the proximal end 32b of the sensing wire 32. When the displacement amount detected part 40 is displaced, the amount of displacement is detected by the displacement amount detecting part 60. A detection signal of the amount of displacement detected by the displacement amount detecting part 60 is output to the outside if necessary.

In the present embodiment, although the distal end of the wire guide 34 of the sensing wire 32, as shown in FIG. 3, is located at a position up to the vicinity of a joint on the proximal end side among the plurality of joints and is adapted to detect the bending amount of a portion in front of this position, the distal end of the wire guide 34 may be extended to the distal end side and be adapted to detect the amount of displacement in front of this distal end side. For example, the distal end of the wire guide 34 is located at a position up to the vicinity of the movable part 12, and detects the amount of rotation of the movable part 12 in front thereof.

In the treatment tool M1 of the present embodiment, the displacement amount detected part 40 is provided on the treatment tool unit 1 side. Meanwhile, the displacement amount detecting part 60 is provided on the drive unit 50 side. Therefore, when the treatment tool unit 1 and the drive unit 50 are coupled together, deviation may occur in the correspondence relationship between the displacement amount detected part 40 and the displacement amount detecting part 60.

However, in the treatment tool M1 of the present embodiment, the sliding direction of the displacement amount detected part 40 is set to the direction parallel to the combined surface 21a of the treatment-tool-unit-side base member 21. Additionally, the displacement amount detecting part 60 can detect the amount of displacement of the displacement amount detected part 40 in a contactless manner. Therefore, even if there is an error, deviation, or the like in a direction along the combined surface 21a, the displacement amount detecting part 60 can precisely detect the amount of displacement of the displacement amount detected part 40 simply by origin adjustment being performed.

Therefore, according to the present treatment tool M1, attachment and detachment of the treatment tool unit 1 with respect to the drive unit 50 can be performed without degrading the detection precision of the amount of displacement of the movable part 12.

In the above embodiment, an example of the displacement amount detected part 40 in which the high-reflection portion 40b and the low-reflection portion 40c are alternately arrayed at regular pitches is shown as an example of the displacement amount detected part 40. However, other displacement amount detected parts can also be adopted. For example, a displacement amount detected part in which slits are formed instead of the high-reflection portion 40b and the low-reflection portion 40c can also be adopted.

Additionally, in the above embodiment, the optical encoder is mentioned as an example of the non-contact type displacement amount detecting part 60. However, a sensor that magnetically detects the amount of displacement can be used as another detecting part. When the magnetic sensor that magnetically detects the amount of displacement is used, a sensor in which magnets are arrayed is used instead of the array of the high-reflection portion 40b and the low-reflection portion 40c of the displacement amount detected part.

Additionally, in the above embodiment, the combination in which the amount of displacement is detected in a digital manner is used as the combination of the displacement amount detected part 40 and the displacement amount detecting part 60. However, the combination of the displacement amount detected part 40 and the displacement amount detecting part 60 that detects the amount of displacement in an analog manner may be used.

Second Embodiment

Next, a treatment tool M2 of a second embodiment of the present invention will be described. In respective embodiments to be described below, the same constituent elements as those of the above-described first embodiment will be designated by the same reference numerals, and duplicate description will be omitted.

Figure 7:
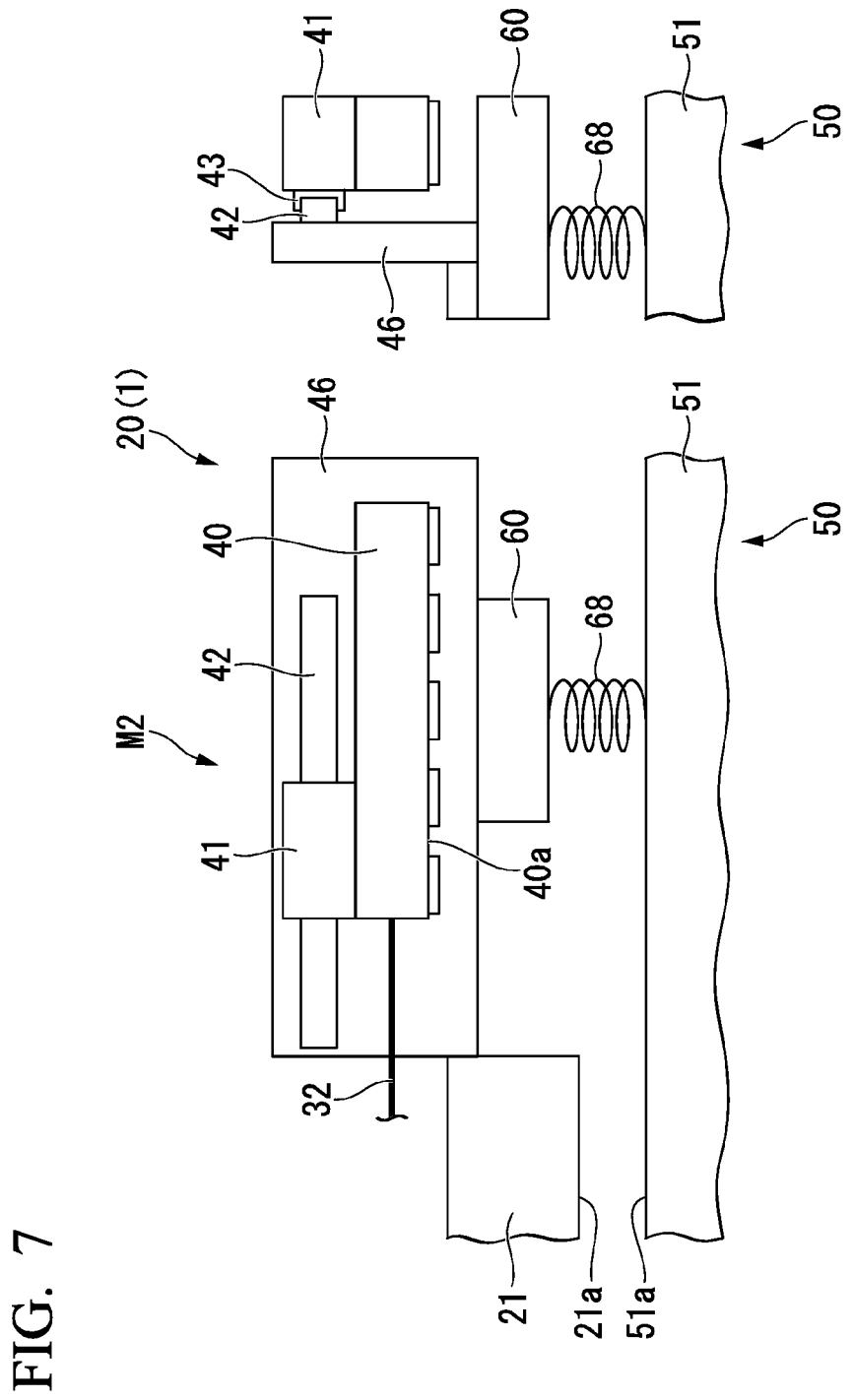
FIG. 7 is a configuration view of essential parts in a treatment tool of a second embodiment of the present invention.

FIG. 7 is a configuration view of essential parts in the treatment tool of the second embodiment of the present invention.

As shown in FIG. 7, in the present treatment tool M2, the displacement amount detecting part 60 is provided so as to be movable with respect to the combined surface 51a of the drive-unit-side base member 51 with a spring 68 of which one end is fixed to the drive-unit-side base member 51. That is, the one end of the spring 68 is fixed to the drive-unit-side base member 51, and the other end of the spring 68 is fixed to the displacement amount detecting part 60. Additionally, the displacement amount detecting part 60 is pressed against an end surface of the bracket 46 by the spring 68. The end surface of the bracket 46 defines the distance between the displacement amount detecting part 60 and the detected surface 40a. The other configuration is the same as that of the first embodiment.

The same effects as those of the above-described first embodiment can also be exhibited even in the present embodiment.

Moreover, in the treatment tool M2 of the present embodiment, the displacement amount detecting part 60 on the drive unit 50 side is pressed against the combined surface 21a of the treatment-tool-unit-side base member 21 when the treatment-tool-unit-side base member 21 and the drive-unit-side base member 51 are coupled together. Therefore, the present treatment tool M2 can prevent any deviation from occurring in the positional relationship between the displacement amount detecting part 60 and the displacement amount detected part 40 in the direction orthogonal to the combined surface 21a. Therefore, the detection precision of the amount of displacement of the movable part 12 does not easily degrade.

In the above embodiment, the displacement amount detecting part 60 is pressed against the combined surface 21a of the treatment-tool-unit-side base member 21 with a biasing force of the spring 68. However, the displacement amount detecting part 60 may be pressed against the combined surface 21a of the treatment-tool-unit-side base member 21 with a magnetic force of a magnet.

Third Embodiment

Next, a treatment tool M3 of a third embodiment of the present invention will be described.

Figure 8:
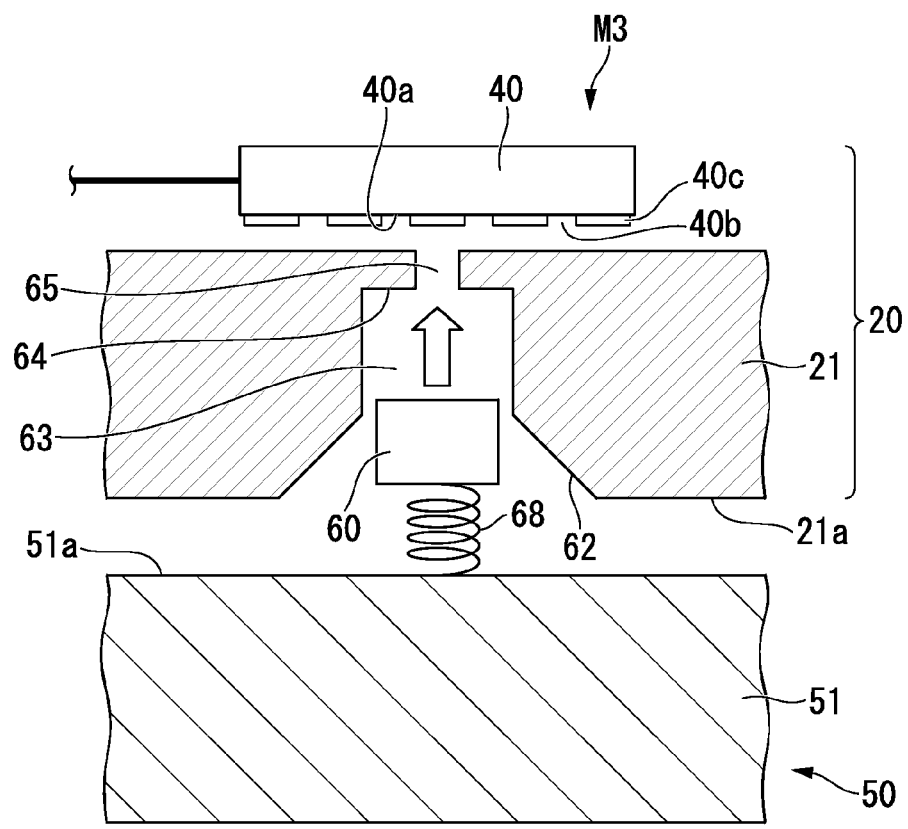
FIG. 8 is a configuration view of essential parts in a treatment tool of a third embodiment of the present invention.

FIG. 8 is a configuration view of essential parts in the treatment tool of the third embodiment of the present invention. As shown in FIG. 8, in the present treatment tool M3, similar to the second embodiment, the displacement amount detecting part 60 is provided so as to be movable in the direction orthogonal to the combined surface 51a of the drive-unit-side base member 51. One end of the spring 68 is fixed to the drive-unit-side base member 51. The displacement amount detecting part 60 is fixed to the other end of the spring 68, and is movable with respect to the drive-unit-side base member 51. Moreover, the displacement amount detecting part 60 is housed in a sliding hole 58 of the drive-unit-side base member 51.

The displacement amount detecting part 60 is biased toward the displacement amount detected part 40 of the treatment tool base part 20 by the spring 68 provided in the drive unit 50. Additionally, a positioning hole 63 of which an inlet is formed as a taper 62 is provided in the treatment tool base part 20 as a positioning portion of the displacement amount detecting part 60. An abutment wall 64 is provided at a deep end of the positioning hole 63. The abutment wall 64 is provided with a through-hole 65.

The same effects as those of the above-described first embodiment can also be exhibited even in the present embodiment.

Moreover, in the treatment tool M3 of the present embodiment, the displacement amount detecting part 60 on the drive unit 50 side is inserted into the positioning hole 63 of the treatment tool base part 20 while being guided by the taper 62 when the treatment-tool-unit-side base member 21 and the drive-unit-side base member 51 are coupled together. The inserted displacement amount detecting part 60 is positioned in a plane parallel to the combined surface 21a of the treatment-tool-unit-side base member 21 with respect to the displacement amount detected part 40 by the position thereof being regulated by a peripheral wall of the positioning hole 63. Additionally, as the distal end of the displacement amount detecting part 60 bumps against an abutment wall 64, the displacement amount detecting part is positioned in the direction orthogonal to the combined surface 21a of the treatment-tool-unit-side base member 21, with respect to the displacement amount detected part 40.

Therefore, the present treatment tool M3 can prevent any positional deviation from occurring between the displacement amount detecting part 60 and the displacement amount detected part 40 in the direction parallel to the combined surface 21a when the treatment-tool-unit-side base member 21 and the drive-unit-side base member 51 are coupled together. Additionally, the present treatment tool M3 can prevent any positional deviation from occurring between the displacement amount detecting part 60 and the displacement amount detected part 40 in the direction orthogonal to the combined surface 21a. Therefore, degradation of the detection precision of the amount of displacement of the movable part 12 is prevented.

Fourth Embodiment

Figure 9:
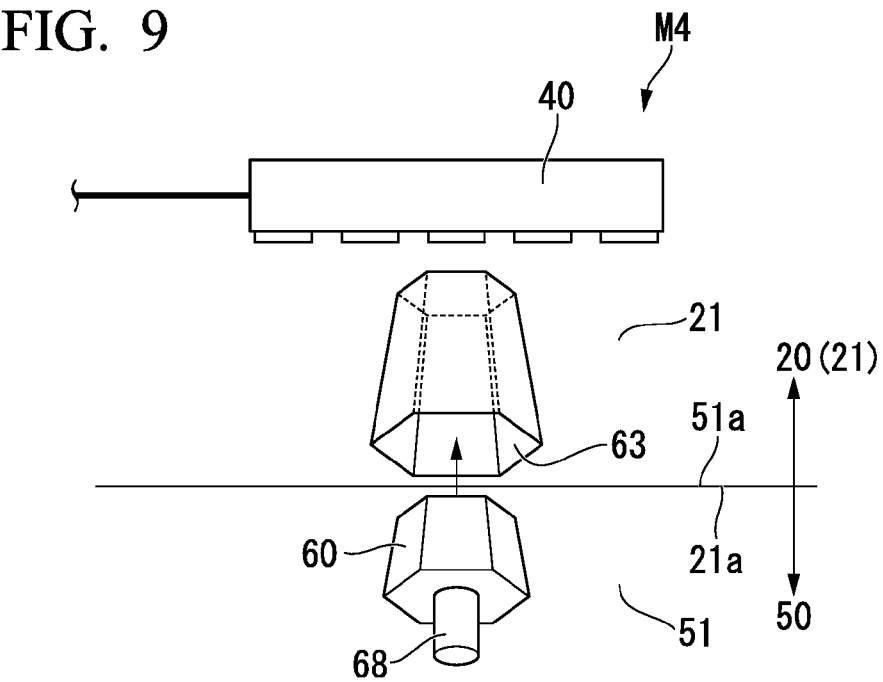
FIG. 9 is a configuration view of essential parts in a treatment tool of a fourth embodiment of the present invention.

Next, a treatment tool M4 of a fourth embodiment of the present invention will be described. FIG. 9 is a configuration view of essential parts in the treatment tool of the fourth embodiment of the present invention. As shown in FIG. 9, in the present treatment tool M4, similar to the second and third embodiments, the displacement amount detecting part 60 is provided so as to be movable in the direction orthogonal to the combined surface 51a of the drive-unit-side base member 51.

The displacement amount detecting part 60 is biased toward the displacement amount detected part 40 of the treatment tool base part 20 by the spring 68 provided in the drive unit 50. Additionally, a tapered polygonal positioning hole 63 of which an inlet is widened is provided in the treatment tool base part 20 as a positioning portion of the displacement amount detecting part 60. Additionally, the shape of an outer peripheral surface of the displacement amount detecting part 60 is formed in a tapered shape that is fitted to the positioning hole 63 with no gap.

The same effects as those of the above-described first embodiment can also be exhibited even in the present embodiment.

Moreover, in the treatment tool M4 of the present embodiment, the displacement amount detecting part 60 on the drive unit 50 side is fitted to the positioning hole 63 of the treatment tool base part 20 when the treatment-tool-unit-side base member 21 and the drive-unit-side base member 51 are coupled together. The fitted displacement amount detecting part 60 is positioned in the plane parallel to the combined surface 21a of the treatment-tool-unit-side base member 21 with respect to the displacement amount detected part 40 by the position thereof being regulated by the peripheral wall of the positioning hole 63. Additionally, the displacement amount detecting part 60 is positioned in the direction orthogonal to the combined surface 21a of the treatment-tool-unit-side base member 21, with respect to the displacement amount detected part 40.

Therefore, the present treatment tool M4 can prevent any positional deviation from occurring between the displacement amount detecting part 60 and the displacement amount detected part 40 in the direction parallel to the combined surface 21a when the treatment-tool-unit-side base member 21 and the drive-unit-side base member 51 are coupled together. Additionally, the present treatment tool M4 can prevent any positional deviation from occurring between the displacement amount detecting part 60 and the displacement amount detected part 40 in the direction orthogonal to the combined surface 21a. Therefore, degradation of the detection precision of the amount of displacement of the movable part 12 is prevented.

Fifth Embodiment

Figure 10:
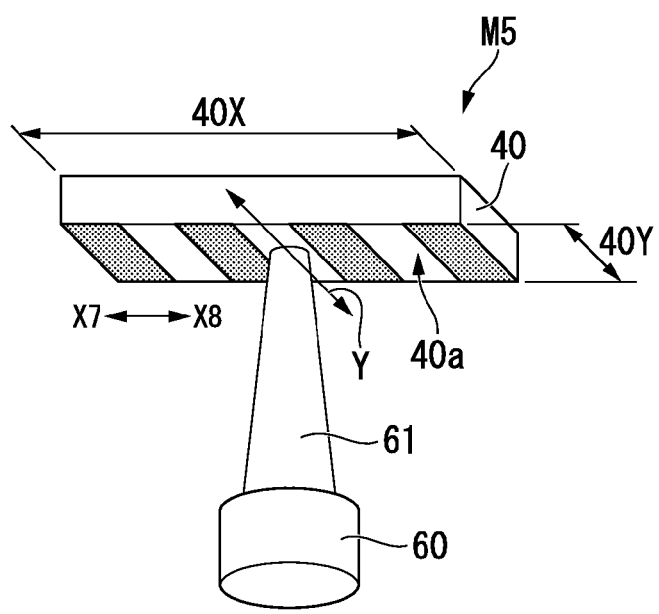
FIG. 10 is a configuration view of essential parts in a treatment tool of a fifth embodiment of the present invention.

Next, a treatment tool M5 of a fifth embodiment of the present invention will be described. FIG. 10 is a configuration view of essential parts in the treatment tool of the fifth embodiment of the present invention. As shown in FIG. 10, the present treatment tool M5 has a feature in terms of the size of the rectangular detected surface 40a of the displacement amount detected part 40. For example, when the size of the detected surface 40a in the sliding direction (directions of arrows X7 and X8) of the displacement amount detected part 40 is defined as a dimension 40X and the size of the detected surface 40a in a direction (direction of arrow Y) orthogonal to the sliding direction of the displacement amount detected part 40 is defined as a dimension 40Y, the dimensions 40X and 40Y are sets to be greater than an expected connection error in a direction along the combined surfaces 21a and 51a when combining the treatment-tool-unit-side base member 21 and the drive-unit-side base member 51 together.

In the present treatment tool M5, even in a case where any deviation occurs in the direction along the combined surfaces 21a and 51a when the treatment-tool-unit-side base member 21 and the drive-unit-side base member 51 are coupled together, the displacement amount detected part 40 and the displacement amount detecting part 60 appropriately correspond to each other. That is, even if any deviation occurs in the direction along the combined surfaces 21a and 51a, the displacement amount detected part 40 is configured such that the detection light 61 from the displacement amount detecting part 60 reaches a suitable position. Therefore, even in the present embodiment, the position detection of the movable part 12 is allowed without being influenced by the positional deviation between the treatment-tool-unit-side base member 21 and the drive-unit-side base member 51.

Sixth Embodiment

Next, a treatment tool M6 of a sixth embodiment of the present invention will be described.

Figure 11:
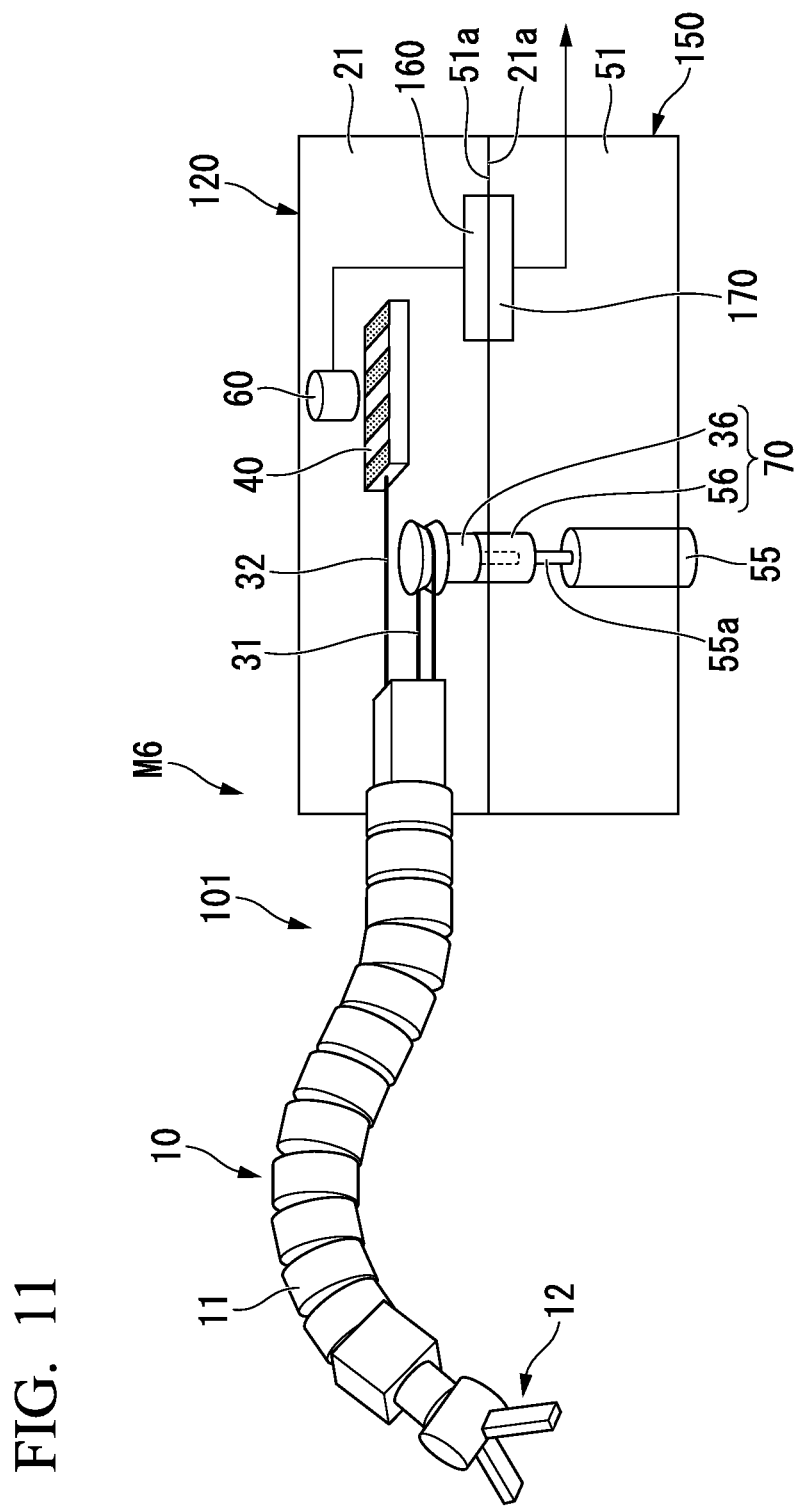
FIG. 11 is a configuration view schematically showing the general outline of a treatment tool of a sixth embodiment of the present invention.
Figure 12:
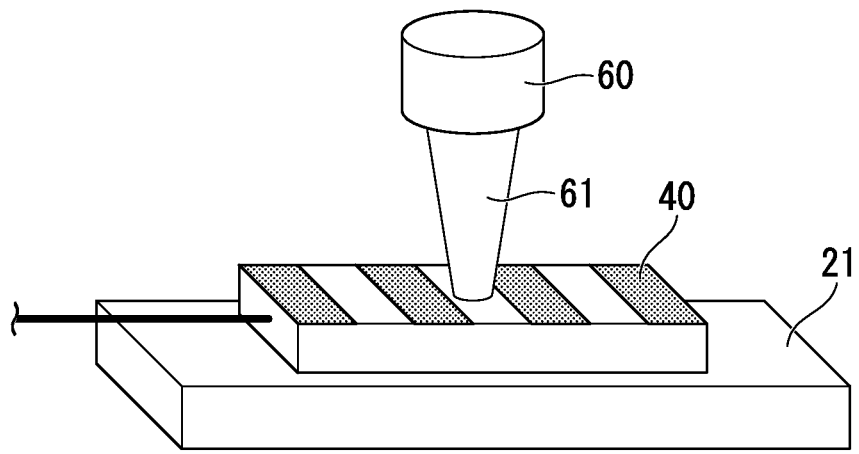
FIG. 12 is a perspective view showing the relationship between the displacement amount detected part and the displacement amount detecting part in the treatment tool of the sixth embodiment of the present invention.

FIG. 11 is a configuration view schematically showing the general outline of the treatment tool of the sixth embodiment of the present invention. FIG. 12 is a perspective view showing the relationship between the displacement amount detected part and the displacement amount detecting part of the treatment tool.

In the above first to fourth embodiments, the displacement amount detecting part 60 is provided on the drive unit 50 side. In contrast, as shown in FIGS. 11 and 12, in a treatment tool unit 101 of the treatment tool M6 of the present embodiment, the displacement amount detecting part 60 is provided not in a drive unit 150 side but in a treatment tool base part 120. Additionally, the treatment tool base part 120 is provided with a transmitting unit 160 that transmits a signal to the displacement amount detecting part 60. Meanwhile, the drive unit 150 is provided with a receiving unit 170 that can receive a detection signal output from the transmitting unit 160 and can take out the detection signal to the outside.

The transmitting unit 160 and the receiving unit 170 are brought into a receivable state when the treatment-tool-unit-side base member 21 is coupled to the drive-unit-side base member 51. A cable type having contact points that are electrically connected to each other when the treatment-tool-unit-side base member 21 is coupled to the drive-unit-side base member 51 can be adopted as the transmitting unit 160 and the receiving unit 170. In addition to this, a wireless type can also be adopted as the transmitting unit 160 and the receiving unit 170.

In the treatment tool M6 of the present embodiment, since both the displacement amount detecting part 60 and the displacement amount detected part 40 are provided in the treatment tool base part 120, a fixed correspondence relationship is obtained regardless of the combination of the treatment tool unit 101 and the drive unit 150. Therefore, the displacement amount detecting part 60 can precisely detect the amount of displacement of the movable part 12, without being influenced by an error or deviation caused by the combination of the treatment tool unit 101 and the drive unit 150.

Although a case where the bending as the displacement of the movable part 12 is taken as an example has been described in the above embodiments, the present invention is not limited to this, and for example, the amount of opening and closing of the gripping part 12A provided in the movable part 12 may be detected as the displacement. In this case, it is preferable to couple the distal end 32a of the sensing wire 32 to the vicinity of the wire 13A of the link 13. Moreover, the displacements of both the bending and the opening and closing may be detected by coupling the distal end 32a of the sensing wire 32 to the movable part 12 (the distal end of the insertion part 11) and the wire 13A, respectively.

Additionally, a mechanism for the movable part 12 may be, for example, a linear motion without being limited to the bending and the opening and closing. Moreover, the position of the movable part 12 is not limited to the distal end of the insertion part 11, and for example, a linear motion mechanism may also be located in the middle of the insertion part 11.

While the preferred embodiments of the present invention have been described and shown above, it should be understood that these are exemplary of the present invention and are not to be considered as limiting. Additions, omissions, substitutions, and other modifications of components can be made without departing from the concept of the present invention.

Additionally, the present invention is not to be considered as being limited by the foregoing description, and is limited only by the scope of the appended claims.

The invention claimed is:

1. A treatment tool comprising:
a treatment tool unit; and
a drive unit which is detachably combined with the treatment tool unit,
wherein the treatment tool unit comprises:
   a movable part that is displaced;
   an insertion part that has the movable part; and
   a driving force transmission member that has a distal end coupled to the movable part, has a proximal end guided to a proximal end side of the insertion part along the insertion part, and transmits a driving force to the movable part to displace the movable part by the driving force being input from the outside to the proximal end;
   a displacement amount transmission member that has a distal end coupled to at least one of the driving force transmission member and the movable part, has a proximal end guided to the proximal end side of the insertion part along the insertion part, and transmits the amount of displacement thereof to the proximal end when the movable part has been displaced;
   a treatment-tool-unit-side base member that has the proximal end side of the insertion part combined therewith;
   a driving force input part that is provided in a treatment-tool-unit-side base member, and inputs the driving force from the outside for displacing the movable part to the proximal end of the driving force transmission member; and
   a displacement amount detected part that is provided at the proximal end of the displacement amount transmission member and is displaced along a given direction by an amount according to the amount of displacement transmitted to the proximal end of the displacement amount transmission member,
wherein the drive unit comprises:
   a driving source that generates a driving force that actuates the movable part; and
   a drive-unit-side base member that supports the driving source and has the treatment-tool-unit-side base member of the treatment tool base part detachably coupled thereto; and
   a displacement amount detecting part that is brought into a state where the displacement amount detecting part detects the displacement amount detected part, and wherein the displacement amount detecting part is brought into a state where a detection signal is outputtable from the drive unit side when the treatment-tool-unit-side base member is coupled to the drive-unit-side base member,
wherein a power transmission joint that detachably couples an output part of the driving source and the driving force input part in a state where power transmission is allowed from the output part of the driving source to the driving force input part when the treatment-tool-unit-side base member is coupled to the drive-unit-side base member, and
is provided between the treatment tool unit and the drive unit.

2. The treatment tool according to claim 1,
wherein the displacement amount detected part is provided so as to be movable along a direction parallel to a combined surface of the treatment-tool-unit-side base member combined with the drive-unit-side base member, and
wherein the displacement amount detecting part is provided as a displacement amount detecting part for detecting the amount of displacement of the displacement amount detected part in a contactless manner with respect to the displacement amount detected part, at a position on the drive unit side that faces the displacement amount detected part when the treatment-tool-unit-side base member and the drive-unit-side base member are coupled together.

3. The treatment tool according to claim 2,
wherein the treatment tool unit is provided with a positioning portion that positions the displacement amount detecting part with respect to the displacement amount detected part, and
wherein the drive unit is provided with a biasing part for biasing and positioning the displacement amount detecting part provided in the drive unit to the positioning portion provided in the treatment tool unit when the treatment-tool-unit-side base member and the drive-unit-side base member are coupled together.

4. The treatment tool according to claim 2,
wherein the treatment tool unit is provided with a positioning portion that positions the displacement amount detecting part with respect to the displacement amount detected part as the displacement amount detecting part provided in the drive unit is fitted to the positioning portion when the treatment-tool-unit-side base member and the drive-unit-side base member are coupled together.

5. The treatment tool according to claim 2,
wherein the size of the displacement amount detected part is set to be greater than an expected connection error in a direction along combined surfaces of the treatment-tool-unit-side base member and the drive-unit-side base member when the treatment-tool-unit-side base member and the drive-unit-side base member are coupled together.

6. The treatment tool according to claim 1,
wherein the displacement amount detecting part is provided at the position of the treatment tool unit that faces the displacement amount detected part,
wherein the treatment tool unit is provided with a transmitting unit for the detection signal from the displacement amount detecting part, and
wherein a receiving unit capable of receiving the detection signal of the displacement amount detecting part from the transmitting unit and outputting the received detection signal is provided at the position of the drive unit where transfer of the detection signal with the transmitting unit is allowed when the treatment-tool-unit-side base member and the drive-unit-side base member are coupled together.

7. The treatment tool according to claim 1, wherein a distance between the displacement amount detected part and the displacement amount detecting part in a state where the treatment-tool-unit-side base member is coupled to the drive-unit-side base member is shorter than a distance between the displacement amount detected part and the displacement amount detecting part in a state where a coupling between the treatment-tool-unit-side base member and the drive-unit-side base member is released.

8. The treatment tool according to claim 1, wherein the displacement amount detecting part is able to be a distance away from the displacement amount transmission member when a coupling between the treatment-tool-unit-side base member and the drive-unit-side base member is released.

9. A treatment tool comprising:
a treatment tool unit which has a treatment tool body part and a treatment tool base part; and
a drive unit which is detachably combined with the treatment tool base part of the treatment tool unit,
wherein the treatment tool body part comprises:
   a movable part that is displaced;
   an insertion part that has the movable part; and
   a driving force transmission member that has a distal end coupled to the movable part, has a proximal end guided to a proximal end side of the insertion part along the insertion part, and transmits a driving force to the movable part to displace the movable part by the driving force being input from the outside to the proximal end; and
   a displacement amount transmission member that has a distal end coupled to at least one of the driving force transmission member and the movable part, has a proximal end guided to the proximal end side of the insertion part along the insertion part, and transmits the amount of displacement thereof to the proximal end when the movable part has been displaced,
wherein the treatment tool base part comprises:
   a treatment-tool-unit-side base member that has the proximal end side of the insertion part combined therewith;
   a driving force input part that is provided in a treatment-tool-unit-side base member, and inputs the driving force from the outside for displacing the movable part to the proximal end of the driving force transmission member; and
   a displacement amount detected part that is provided at the proximal end of the displacement amount transmission member and is displaced along a given direction by an amount according to the amount of displacement transmitted to the proximal end of the displacement amount transmission member,
wherein the drive unit comprises:
   a driving source that generates a driving force that actuates the movable part; and
   a drive-unit-side base member that supports the driving source and has the treatment-tool-unit-side base member of the treatment tool base part detachably coupled thereto,
wherein a power transmission joint that detachably couples an output part of the driving source and the driving force input part in a state where power transmission is allowed from the output part of the driving source to the driving force input part when the treatment-tool-unit-side base member is coupled to the drive-unit-side base member, and
a displacement amount detecting part that is brought into a state where the amount of displacement of the displacement amount detected part is detectable and that is brought into a state where a detection signal is outputtable from the drive unit side when the treatment-tool-unit-side base member is coupled to the drive-unit-side base member
are provided between the treatment tool unit and the drive unit,
wherein the displacement amount detected part is provided so as to be movable along a direction parallel to a combined surface of the treatment-tool-unit-side base member combined with the drive-unit-side base member, and
wherein the displacement amount detecting part is provided as a displacement amount detecting part for detecting the amount of displacement of the displacement amount detected part in a contactless manner with respect to the displacement amount detected part, at a position on the drive unit side that faces the displacement amount detected part when the treatment-tool-unit-side base member and the drive-unit-side base member are coupled together, wherein the treatment tool unit is provided with a positioning portion that positions the displacement amount detecting part with respect to the displacement amount detected part, and
wherein the drive unit is provided with a biasing part for biasing and positioning the displacement amount detecting part provided in the drive unit to the positioning portion provided in the treatment tool unit when the treatment-tool-unit-side base member and the drive-unit-side base member are coupled together.

10. The treatment tool according to claim 9,
wherein the treatment tool unit is provided with a positioning portion that positions the displacement amount detecting part with respect to the displacement amount detected part as the displacement amount detecting part provided in the drive unit is fitted to the positioning portion when the treatment-tool-unit-side base member and the drive-unit-side base member are coupled together.

11. The treatment tool according to claim 9,
wherein the size of the displacement amount detected part is set to be greater than an expected connection error in a direction along combined surfaces of the treatment-tool-unit-side base member and the drive-unit-side base member when the treatment-tool-unit-side base member and the drive-unit-side base member are coupled together.

12. The treatment tool according to claim 9,
wherein the displacement amount detecting part is provided at the position of the treatment tool unit that faces the displacement amount detected part,
wherein the treatment tool unit is provided with a transmitting unit for the detection signal from the displacement amount detecting part, and
wherein a receiving unit capable of receiving the detection signal of the displacement amount detecting part from the transmitting unit and outputting the received detection signal is provided at the position of the drive unit where transfer of the detection signal with the transmitting unit is allowed when the treatment-tool-unit-side base member and the drive-unit-side base member are coupled together.

* * * * *